United States Patent [19]
Green

[11] 3,970,841
[45] July 20, 1976

[54] METHOD AND APPARATUS FOR DUAL RESOLUTION ANALYSIS OF A SCENE

[76] Inventor: James E. Green, Box 734, Fayetteville, Tenn. 37334

[22] Filed: Nov. 25, 1974

[21] Appl. No.: 526,896

[52] U.S. Cl. .............................. 250/201; 250/208; 250/222 PC; 250/578; 356/39
[51] Int. Cl.² .................. H01J 39/12; G01N 33/16
[58] Field of Search .............. 356/39, 40; 250/578, 250/548, 201, 203, 208, 209, 222 PC; 235/92 PC; 350/37, 40

[56] References Cited
UNITED STATES PATENTS

| | | | |
|---|---|---|---|
| 3,448,271 | 6/1969 | Aldrich et al. | 250/203 |
| 3,614,449 | 10/1971 | Ward | 250/203 |
| 3,804,976 | 4/1974 | Gard | 250/203 X |
| 3,864,564 | 2/1975 | Adkins | 250/201 |

*Primary Examiner*—Eugene La Roche
*Attorney, Agent, or Firm*—Richard J. Birch

[57] ABSTRACT

A method and apparatus for analyzing a scene at a low resolution until an object of interest is detected. Thereafter, the object of interest is analyzed at a higher resolution while continuing to analyze the scene at the low resolution. In the preferred embodiment, the scene compromises a blood sample and the objects of interest are blood cells.

22 Claims, 7 Drawing Figures

FIG. I

METHOD AND APPARATUS FOR DUAL RESOLUTION ANALYSIS OF A SCENE

BACKGROUND OF THE INVENTION

The present invention relates to scene analysis apparatus and methods and more particularly, to a method and apparatus for analyzing a scene at two different resolutions.

In many areas of particle analysis, such as, blood cell analysis or pap smear analysis, the particles of interest are widely distributed in a field and are surrounded by many particles of no interest at all. For example, white blood cells may be surrounded by hundreds of red blood cells while cancerous or dysplastic cervical cells may be surrounded by tens-to-thousands of normal cervical cells and debris.

It is desirable to analyze only the particles of interest in the scene. This can be done by analyzing all of the objects in order to exclude the unwanted objects. However, this technique is very time-consuming and therefore relatively impractical from a commercial standpoint. Alternately, one can use a single sensor to search for particles of interest at a low resolution and then switch the sensor to a higher resolution for analysis when a particle of interest is found in the sample. However, this method requires mechanical or electrical switching of the analysis resolution with a concomitant limitation of a single mode of operation at any given time.

It is accordingly, a general object of the invention to provide a method and apparatus for scene analysis which overcomes the limitations of the prior art systems.

. It is specific object of the invention to provide a method and apparatus for dual resolution analysis of a scene.

In the accomplishment of these objects, two sensors are employed; one covering a large field at a low resolution and the other covering a small field at a higher resolution. The low resolution field of view (large field) is located in a known relationship to the higher resolution field of view (the small field). Given the known relationship of the resolution fields, when an object of interst is detected in the low resolution field, it can be moved into the higher resolution field for further detailed analysis while continuing the analysis of the scene or sample at the low resolution to detect any other objects of interest. Thus a plurality of degrees of resolution analysis can occur substantially simultaneously.

The objects and features of the invention can best be understood from a detailed description of a preferred embodiment thereof, selected for purposes of illustration and shown in the accompanying drawings, in which.

Figure 1:
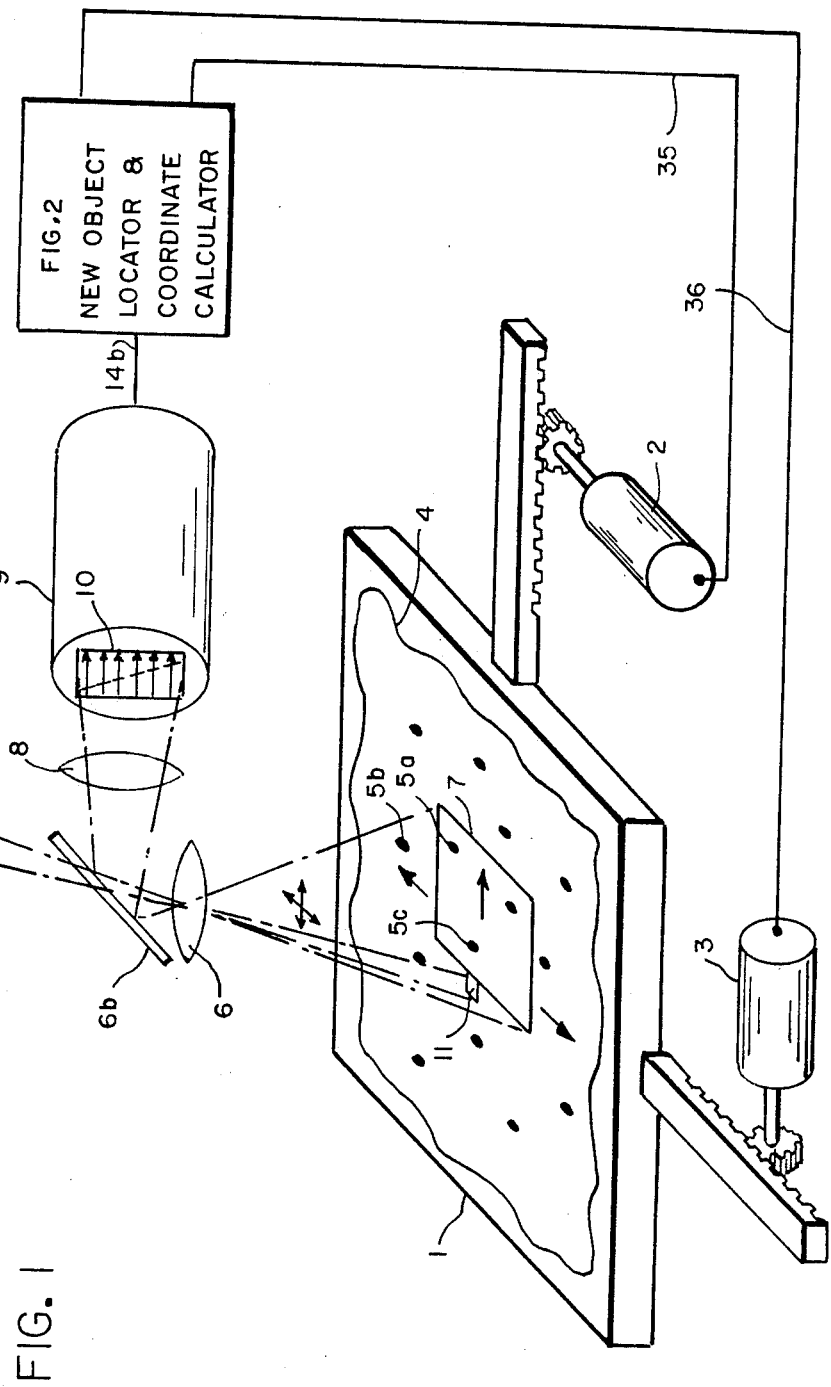
FIG. 1 is a diagrammatic, perspective view of a dual resolution, analysis apparatus constructed in accordance with the present invention.

Turning now to the drawings, FIG. 1 illustrates in diagrammatic form and perspective view, the dual resolution, analysis apparatus of the present invention. A sample carrier 1, which can be moved in both the X and Y directions by means of drive motors 2 and 3, contains a sample 4 which has a plurality of objects of interest 5a, 5b and 5c. In the blood cell embodiment, the sample carrier 1 normally comprises a glass slide upon which the blood sample 4 is spread in a conventional manner. It will be appreciated that the blood sample will contain many red blood cells and a number of dispersed white blood cells of interest, i.e., cells 5a, 5b and 5c etc.

A primary optical objective 6, such as a microscope objective, forms an image of an area of the sample. The area of the sample which is designated "a low resolution field" 7 is imaged by the primary objective 6 beam splitter 6b and a low resolution secondary optic 8 onto a low resolution sensor 9. The image of the low resolution field 7 on the low resolution sensor 9 is indicated by the reference numeral 10. A relatively smaller area of the sample, termed a "higher resolution field" 11, is imaged by the primary objective 6 and a secondary high resolution optic 12 onto a high resolution sensor 13. The high resolution image on the high resolution sensor 13 is identified by the reference numeral 14.

The low and high resolution sensors 9 and 13, respectively, are conventional opto-electrical image scanners. For example, the opto-electrical scanning sensors can comprise a television camera, image dissector, photodiode array, or the like. The optoelectrical sensors convert the respective images into electrical signals in a well known manner.

Figure 4:
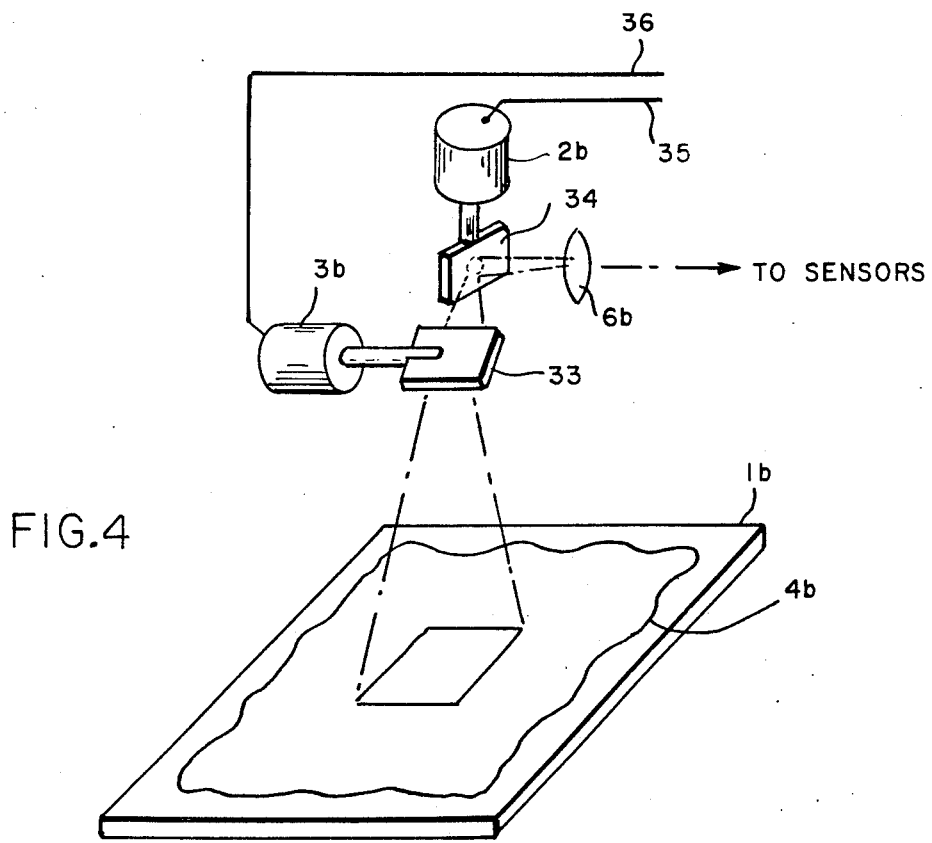

In the present invention, the low resolution signal output from sensor 9 appears on line 14b and is used to establish the position of an object of interest (white cell) such as 5a, 5b or 5c relative to the higher resolution field 11, so that appropriate signals can be generated to move the object of interest into the higher resolution field. In the embodiment illustrated in FIG. 1, the object of interest is moved into the higher resolution field 11 by moving the sample carrier 1 in the X and Y directions by means of drive motors 2 and 3. It will be appreciated that the equivalent relative movement can be achieved by moving the optical system and leaving the sample carrier fixed. Such an arrangement is illustrated in FIG. 4 and will be discussed subsequently.

Figure 2:
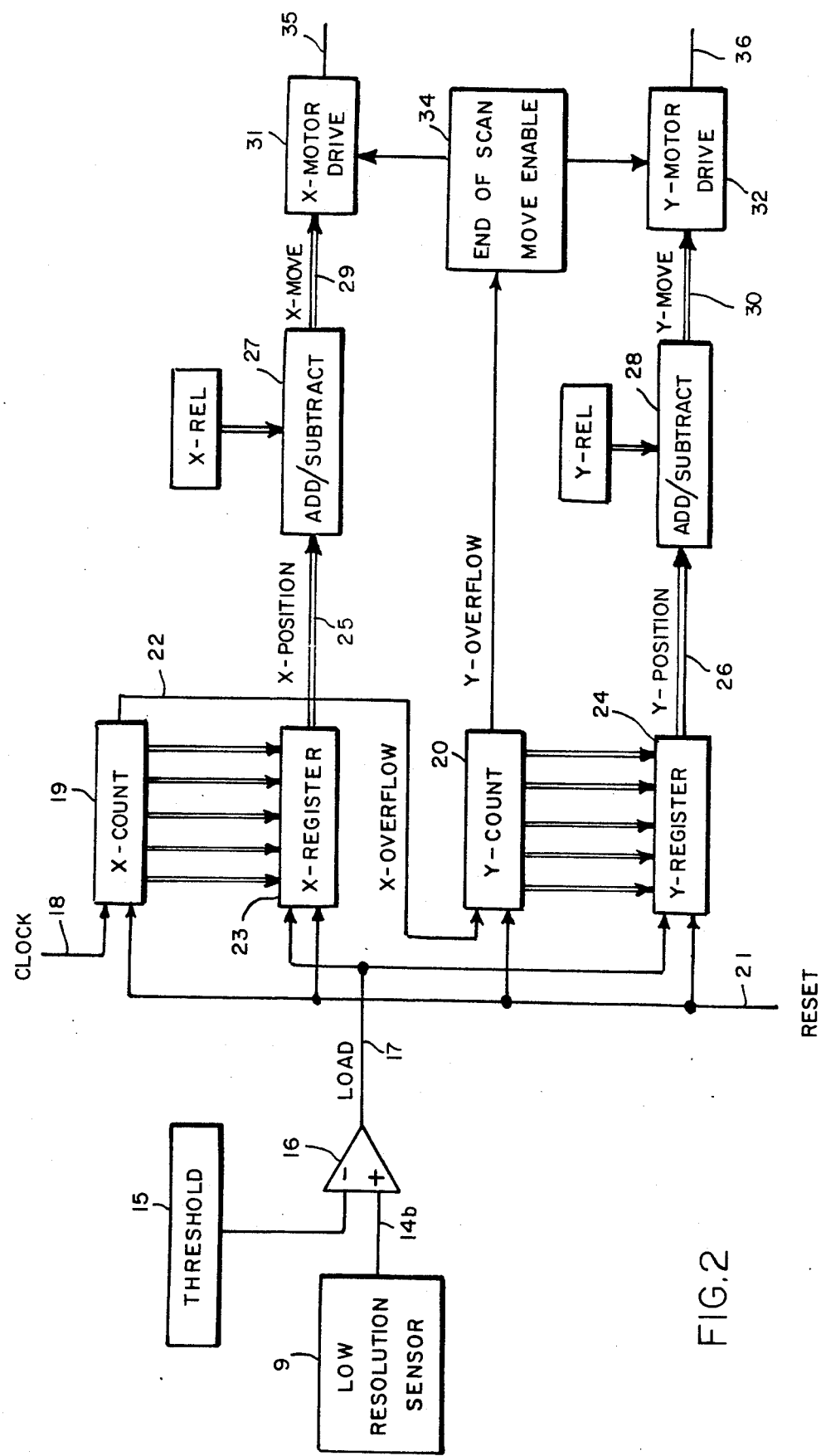
FIG. 2 is a block diagram of the electrical circuitry for locating an object of interest in the scene and determining the coordinates thereof.

Representative circuitry for locating the new object of interest, calculating its coordinates and producing appropriate output signals for actuating the drive motors 2 and 3 to move the object of interest into the higher resolution field 11 is depicted in block diagram form in FIG. 2. The low resolution sensor signal output on line 14b is compared with a preset threshold 15 in comparator 16. In this example, the densities of the objects of interest are higher than the surrounding sample. Thus, the threshold is fixed so that when the low resolution signal output from sensor 9 exceeds the threshold, the dual resolution scanner is assumed to have encountered an object of interest. This condition is indicated by a signal appearing on the comparator output line 17.

Assuming that the low resolution scanner 9 scans in a faster fashion and has 64 × 64 resolution elements (resels), the position of the scanner can be tracked by means of 6 bit X and Y counters 19 and 20 respectively. The X and Y counters are reset by means of reset line 21 before the beginning of each scan. During the scan, clock line 18 increments X counter 19 each time the scanner senses one resel on a horizontal scan line. At the end of each horizontal scan line, the X counter overflows and the overflow signal, on overflow line 22, is used to increment the Y counter 20.

Associated with the X and with Y counters 19 and 20 are corresponding X and Y registers 23 and 24, respectively. The X register 23 is connected to the X counter and the Y register is connected to the Y counter so that when the output from comparator 16 (a "load" signal) is present, the contents of the X counter are transferred to the X register and the contents of the Y counter are transferred to the Y register. Thus, when an object of interest is detected by the comparator 16, the position of that particular object in the low resolution field 7 is stored in the X and Y registers 23 and 24.

The outputs of the X and Y registers appear on output busses 25 and 26. The two output busses feed into corresponding add/subtractors 27 and 28 in which the position of the higher resolution field 11 relative to the low resolution field 7 is subtracted (or added as the case may be) to produce the proper X-move and Y-move signals on output lines 29 and 30. The X and Y motor drive circuitry 31 and 32 transforms the X and Y move signals into electrical signals appropriate to produce the movements represented by the X-move and the Y-move signals.

It should be noted that the FIG. 2 circuitry will have stored the position of the last object in the low resolution field 7 at the end of a scan. However, it will be appreciated that it is possible to inhibit the load signals after the first encountered object of interest so that the position of the first object is saved instead of the last object. The Y-overflow from Y counter 20 is used to inhibit the command of the motor movements through an "end of scan move enable" circuit 34 until the final change in the X and Y registers 23 and 24.

Figure 3:
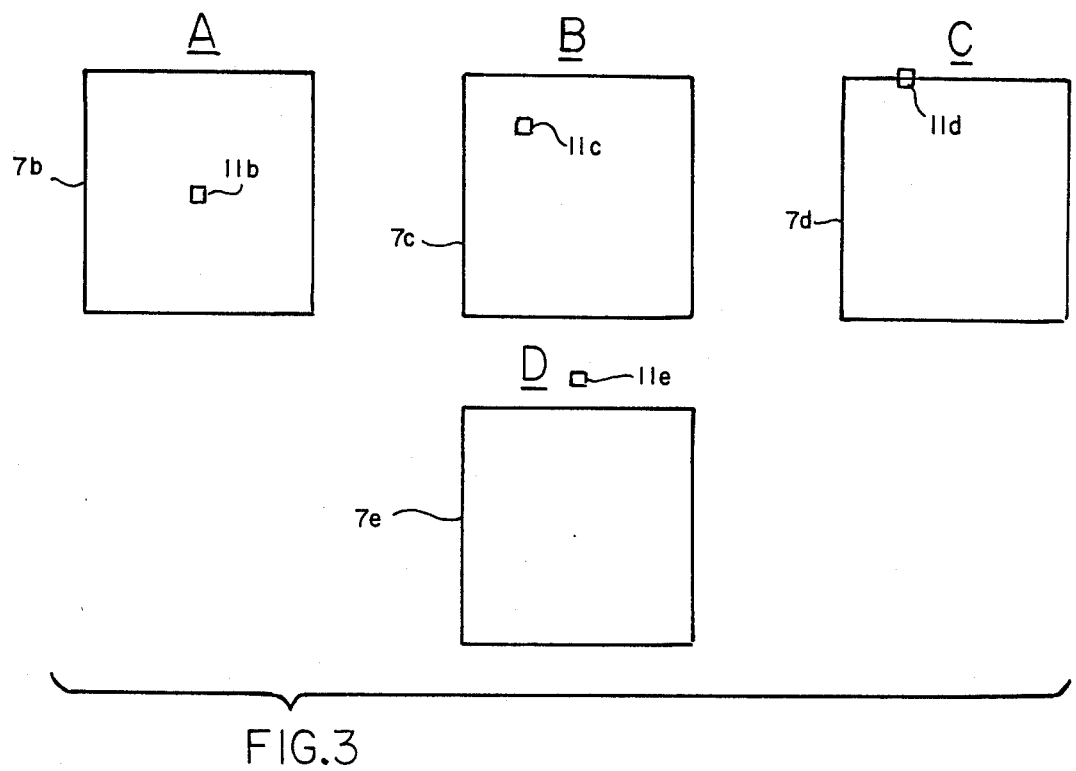
FIGS. 3A through 3D illustrate various relationships between the low resolution field and the higher resolution field; and, FIG. 4 is another diagrammatic view illustrating an alternative embodiment of the dual resolution analysis apparatus.

It should also be observed that the relative position of the higher resolution field 11 with respect to the low resolution field 7 as shown in FIG. 1 is only one of a number of possible positions. FIG. 3 illustrates some of the possible relative positions for the two resolution fields. In FIG. 3A, the higher resolution field 11b is shown positioned at the center of the low resolution field 7. Other locations within the low resolution field can be employed as illustrated in FIG. 3B. The higher resolution field also can partially overlap the low resolution field as illustrated in FIG. 3C or be located entirely outside of the low resolution field as depicted in FIG. 3D. These four arrangements are not intended to be exhaustive, but should be construed as being merely illustrated of a large number of possible arrangements.

It has been mentioned previously that it is not necessary to physically move the sample carrier 1 in order to move an object of interest into the higher resolution field. Looking at FIG. 4, the sample carrier is identified as 1b and the sample as 4b. Drive motors 2b and 3b are employed to drive movable mirrors 33 and 34 which change the area of the sample 4b scanned by the high and low resolution fields without physically moving the sample. Generally, this particular configuration is practical only if the working distance of the primary optical objective 6b is sufficient to allow the mirrors to be conveniently positioned between it and the sample while maintaining relatively uniform focus.

It will be appreciated that the relative movement of higher resolution field with respect to the object of the interest can be accomplished either with or without a corresponding relative movement of the low resolution field 7. In the preferred embodiment, both the low and high resolution fields are moved relative to the object of interest to bring the object of interest into the higher resolution field. However, in the preferred embodiment there is no relative movement between the two resolution fields during the relative movement of the object of interest into the higher resolution field.

The output from the higher resolution sensor 13 is applied to a suitable object analysis means 37. One such analysis means is described in my corresponding application, Ser. No. 286,043, filed Sept. 5, 1972, for ANALYSIS METHOD AND APPARATUS UTILIZING COLOR ALGEBRA AND IMAGE PROCESSING TECHNIQUES, now U.S. Pat. No. 3,851,156.

Having described in detail a preferred embodiment of my invention, it will now be apparent to those skilled in the art that numerous modifications can be made therein without departing from the scope of the invention as defined in the appended claims.

What I claim and desire to secure by Letters Patent of the United States is:

1. A dual resolution sample scanning apparatus comprising:
    means for positioning a sample;
    a first opto-electrical image scanning means producing an output signal when a sample object is encountered during scanning;
    a second opto-electrical image scanning means for producing output signals representative of a scanned image;
    optical means for imaging a low resolution sample field on said first opto-electrical image scanning means and a higher resolution sample field on said second opto-electrical image scanning means;
    means responsive to the output signal from said first opto-electrical image scanning means for moving the higher resolution sample field relative to the sample to bring the encountered sample object into the higher resolution field for scanning by said second opto-electrical image scanning means while the first opto-electrical image scanning means continues to scan the low resolution field to detect any other objects in the sample, said continuing low resolution field scan being performed without moving the sample relative to at least one of said resolution fields; and,
    utilization means responsive to the output signals from said second opto-electrical image scanning means.

2. The apparatus of claim 1 wherein said sample positioning means includes an X-Y movable sample support means and said output signal responsive moving means includes X and Y drive means for moving said sample support means.

3. The apparatus of claim 1 wherein said at least one resolution field is the low resolution field.

4. The apparatus of claim 1 wherein said at least one resolution field is the higher resolution field.

5. The apparatus of claim 1 wherein said continuing low resolution scanning is performed without moving the sample relative to low and higher resolution fields.

6. The apparatus of claim 1 where said optical means for imaging said low and higher resolution sample fields has an optical path for the low resolution sample field and an optical path for the higher resolution sample fields.

7. The apparatus of claim 6 wherein said optical paths have a common portion.

8. The apparatus of claim 1 wherein said output signal responsive moving means moves both the low and higher resolution sample fields relative to the sample.

9. The apparatus of claim 8 wherein said moving means moves both the low and higher resolution sample fields relative to the sample without altering the relative relationship of the two fields with respect to each other.

10. The apparatus of claim 9 wherein the higher resolution sample field is positioned within the low sample resolution field.

11. The apparatus of claim 9 wherein the higher sample resolution field and the low sample resolution field partially overlap.

12. The apparatus of claim 9 wherein the higher resolution sample field is positioned outside of the low resolution sample field.

13. A dual resolution scanning apparatus comprising:
means for positioning a sample;
means for scanning a positioned sample at a low resolution, said low resolution scanning means having a low resolution field of view;
means for detecting when a sample object is encountered during the low resolution scan;
means for scanning an encountered object at a higher resolution, said higher resolution scanning means having a higher resolution field of view;
means responsive to said object detection means for initiating the object scanning by said high resolution scanning means while said low resolution scanning means continues to scan the sample to detect any other objects in the sample without moving the sample relative to at least one of said resolution fields of view.

14. The apparatus of claim 13 wherein said at least one resolution field is the low resolution field.

15. The apparatus of claim 13 wherein said at least one resolution field is the higher resolution field.

16. The apparatus of claim 13 wherein said continuing low resolution scanning is performed without moving the sample relative to low and higher resolution fields.

17. A method for dual resolution scanning of a sample comprising the steps of:
scanning a low resolution field of the sample until an object is detected; and thereafter,
scanning a higher resolution field containing the detected object while continuing scanning of the low resolution field to detect any other objects in the sample, said continuing low resolution scanning being performed without moving the sample relative to at least one of said resolution fields.

18. The method of claim 17 wherein said at least one resolution field is the low resolution field.

19. The method of claim 17 wherein said at least one resolution field is the higher resolution field.

20. The method of claim 17 wherein said continuing low resolution scanning is performed without moving the sample relative to low and higher resolution fields.

21. The method of claim 17 further comprising the step of moving the higher resolution field relative to the sample to bring each detected object into the higher resolution field.

22. The method of claim 21 further comprising the step of moving both the low and higher resolution fields relative to the sample while maintaining the same relative position with respect to each other.

* * * * *